United States Patent [19]

Rosengart

[11] Patent Number: 4,838,850
[45] Date of Patent: Jun. 13, 1989

[54] ELECTROMEDICAL TREATMENT APPARATUS

[76] Inventor: Henning Rosengart, Nevadavej 8, Slagelse, Denmark, 4200

[21] Appl. No.: 51,261

[22] Filed: May 7, 1987

Related U.S. Application Data

[63] Continuation of Ser. No. 627,884, Jul. 3, 1984, abandoned, which is a continuation of Ser. No. 385,656, filed as PCT SE80/00241 on Oct. 3, 1980, published as WO82/01135 on Apr. 15, 1982, abandoned.

[51] Int. Cl.[4] ............................................. A61B 17/52
[52] U.S. Cl. ..................................................... 600/14
[58] Field of Search ................ 128/1.3, 1.5; 600/9, 600/13–15

[56] References Cited

U.S. PATENT DOCUMENTS

| | | | |
|---|---|---|---|
| 3,658,051 | 4/1972 | MacLean | 128/1.5 |
| 3,842,841 | 10/1974 | Brighton et al. | 128/419 F |
| 3,890,953 | 6/1975 | Kraus et al. | 128/1.5 |
| 3,893,462 | 7/1975 | Manning | 128/1.5 X |
| 3,915,151 | 10/1975 | Kraus | 128/1.5 |
| 4,056,097 | 11/1977 | Maass | 128/1.5 |
| 4,095,588 | 6/1978 | Goldman et al. | 128/1.5 |
| 4,105,017 | 8/1978 | Ryaby et al. | 128/1.5 |
| 4,233,965 | 11/1980 | Fairbanks | 128/1.5 |
| 4,266,532 | 5/1981 | Ryaby et al. | 128/1.5 |
| 4,300,545 | 11/1981 | Goodman et al. | 128/200.14 |
| 4,315,503 | 2/1982 | Ryaby et al. | 128/1.5 |

OTHER PUBLICATIONS

Mansfield et al., NMR Imaging in Biomedicine, Academic Press, N.Y., 1982, pp. 297–313.

Primary Examiner—Francis Jaworski
Assistant Examiner—John C. Hanley
Attorney, Agent, or Firm—Holman & Stern

[57] ABSTRACT

An electromedical apparatus including a magnetic field generator and an electric field generator adapted for generation of perpendicular fields and for application of the generated fields transversely to the major blood vessels of an afflicted body portion induces helical movement of charged particles in the tissues and increased blood flow. The apparatus further includes electrical and magnetic lens systems for concentrating the electrical and magnetic flow generated by the apparatus.

7 Claims, 2 Drawing Sheets

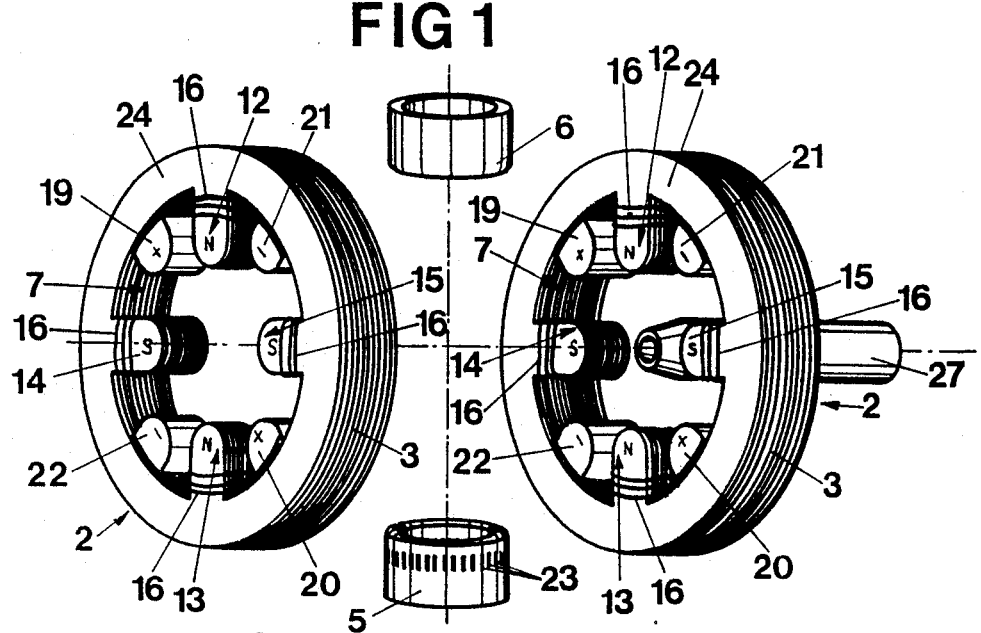
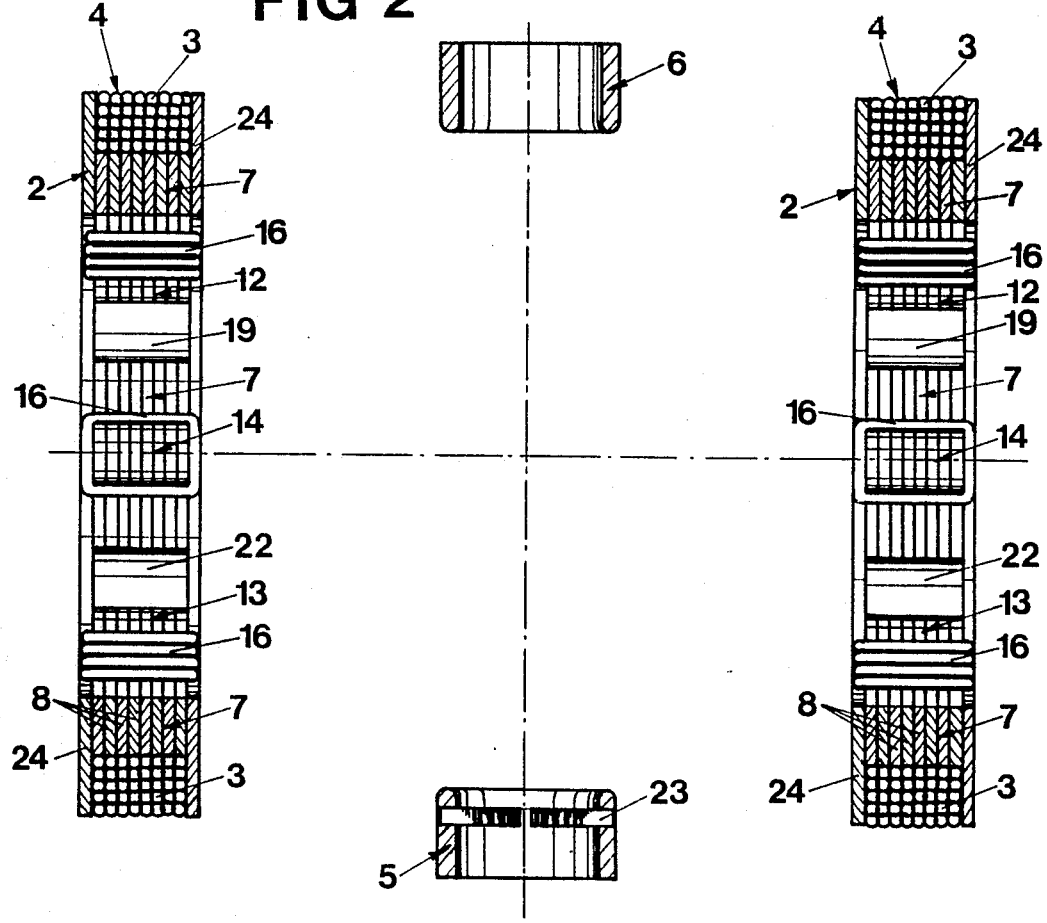

ELECTROMEDICAL TREATMENT APPARATUS

This is a continuation of application Ser. No. 627,884, filed July 3, 1984, now abandoned, which in turn is a continuation of Ser. No. 385,656 filed as PCT SE80/00241 on Oct. 3, 1980, published as WO82/01135 on Apr. 15, 1982, now abandoned.

The present invention refers to an electromedical treatment apparatus for treatment of biological tissue, preferably for speeding up the healing process in a part of a body as for example a leg or an arm, and of the kind that at least generates partly a magnetic and partly an electric field of force in a treatment zone, comprising an electric field generator adapted to generate an electric field of force directed essentially towards and at right angles to the blood-vessels of the object of treatment and within the treatment zone.

BACKGROUND OF THE INVENTION

A large part of the economic and personnel resources today's medical service consume is used for treatment of patients with long lasting illness periods. As an example we can mention the treatment of fractures such as a fractured thigh bone, treatment of rheumatism and patients with neurologic movement handicaps and long term therapy patients with slow-heating infected wounds etc. For this reason it is not least of economical value, but even for reducing personal suffering, of great importance to point out and use medical methods and equipment which speed up and support the healing processes.

It has been known for a long time that magnetic and electric fields affect biological tissue. Injuries and diseases have been treated with varying result. Magnetic and electrical fields have been applied against the diseased or wounded body part and then one has hoped for the best. An example of this kind of treatment apparatus is described in the U.S. Pat. No. 3,915,151. It is primarily adapted for treatment of broken bones and uses preferably flat coils for generation of a magnetic field whose flow is arranged longitudinally with the treatment object, i.e. parallel to a leg or an arm. Besides a magnetic field is in one embodiment an electrostatic field introduced. This is achieved by two diametrically opposite electrodes, to which a voltage with relatively high potential difference is supplied. An electric field is hereby achieved which flows through the treatment object essentially at a right angles to the flow of the magnetic field. By supplying a voltage, whose amplitude fluctuates regularly, the electrically charged particles in the treatment area are brought into an oscillating movement. Due to the magnetic and electric fields flow directions, the charged particles oscillate only at right angles to the skeletal structure and thus perpendicular to the main blood flow of the treatment object. The venous bloodflow, i.e. the blood flow toward the heart, is thereby not affected by this treatment apparatus.

CHARACTERISTICS AND OBJECTS OF THE INVENTION

The object of the present invention is to accelerate the healing process in biological tissue by bringing the electrically charged particles in the actual tissue into a helical movement which supports the metabolism in the tissue and increases the volume of the blood flow. Further objects are to treat rheumatics and patients with circulatory disturbances as well as to prevent thrombosis developing. Also patients with neurological disturbances and diseases such as neurologically caused movement disturbances should further be treated with success. The invention should also be easy and safe to use and in the future reduce the resource needs within the medical service. This is achieved by a magnetic field generator, incorporating at least one solenoid, arranged to generate a magnetic field with a regularly varying field strength in the treatment zone, which field in the treatment zone is directed substantially transversely partly to the electric field and partly to the main blood vessels of the treatment object and that at least one magnetic lens system and one electric lens system is arranged to cooperate and to homogenize as well as concentrate the magnetic field generated by the solenoid in the treatment zone.

BRIEF DESCRIPTION OF THE DRAWING

The invention will here below be described in an embodiment with reference to the attached drawings.

FIG. 1 illustrates a side view in perspective of the electromedical treatment apparatus of the invention, FIG. 2 illustrates a vertical section through the apparatus of FIG. 1;

DETAILED DESCRIPTION OF THE INVENTION

Figure 3:
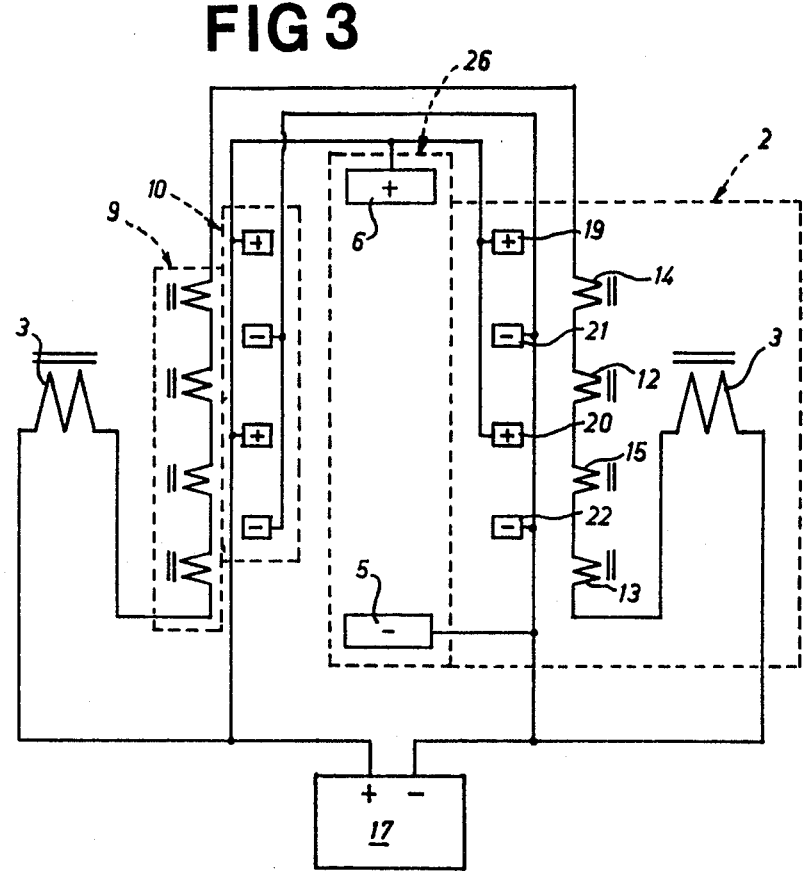
FIG. 3 illustrates an electrical circuit diagram of the invention.

In FIG. 1 is shown schematically a side view of the electromedical treatment apparatus generally indicated at 1 according to the invention. The apparatus 1 includes are mainly two ringshaped lens systems 2 coaxially arranged horizontally and at some distance from one another. Each lens system 2 is at its circumference equipped with a solenoid 3. These solenoids 3 are electrically connected in series and form together a magnetic field generator 4 (FIG. 2). Between the lens system 2 is a lower and an upper field electrode 5, 6 arranged in such way, that an imaginary central axis in each field electrode 5, 6 coincides with each other. The hypothetical central axis of the field electrodes 5, 6 intersects a hypothetical central axis of the lens system 2 perpendicular and at essentially the same distance from each lens system 2. The lenssystems 2 and the field electrodes 5, 6 are arranged on a way that each of them can manually be adjusted in horizontal and vertical line with respect to each other. This arrangement permits the center of the treatment apparatus 1, i.e., the treatment zone between the lens system 2 and the field electrodes 5, 6 to be adjusted to a larger or a smaller size and in this way be adapted to the size of the object to be treated, for example it can be made smaller if an object such as an ankle is to be treated, or larger when a femur is to be treated.

Each of the lens systems 2 included in the treatment apparatus 1 consists essentially of a ringshaped core 7, built up of transformer core sheets 8. These sheet metal lamina, of for example silicon alloyed iron, are in a conventional way isolated from each other and tightly packed in the longitudinal axial direction of the lens system 2. In the defined inner space of each ringshaped core 7 is arranged one magnetic lens 9 and one electric lens 10. The elements 12–15, 19–22 included in each lens 9, 10 can either be attached at the inner surface of the ringformed core 7 or in another way freely be arranged inside the ringformed core 7.

At the circumference of the lens system 2, i.e., at the surface directed off center of the ringformed core 7, is arranged a solenoid 3. The solenoid 3 consists of an isolated copper coiling whose wire diameter is adjusted to the maximum current which is to be introduced to the solenoid 3. To keep the coils of the solenoids 3 in place two side pieces 24 of dielectric material are arranged at each side surface of the lens system 2. To maintain a strong enough magnetic field of force a number of wiring turns may be necessary. Both of the solenoids 3 included in the treatment apparatus are electrically connected in series so that a homogenous magnetic field is maintained in the treatment zone.

The magnetic lens 9 arranged in the lens system 2 is of the so called square pole type and contains four lens elements 12-15 each of which forms a magnetic pole. The preferably cylindrical shaped lens elements 12-15, which for example can be punched in the same material as the ringshaped core 7, are located symmetrically along the inner surface of the core 7 in such a way that the two lens elements 12, 13 which form the north poles and the two lens elements 14, 15 which form the south poles are arranged in pairs diametrically opposite each other. The lens elements 12-15 are, inward the center of the magnetic lens 9 turned part, hyperbolically formed so that a more homogenous magnetic field of force in the center of the magnetic lens 9 is maintained. Around each lens element 12-15 are arranged solenoids 16 in such a manner that each solenoid 16 hypothetical central axis coincides at one and the same point in the center of the lens system 2.

The solenoids 16 are connected electrically in a way that two diametrically arranged lens elements 14, 15 work as south poles and the other two as north poles. The solenoids 16 included in the magnetic lens 9 can be electrically connected in series and connected to a voltage unit 17 (FIG. 3). The main purpose of the magnetic lens 9 is to converge electrically charged particles which are in or pass through the magnetic lens 9. Its function should, however, be seen in relation to other included parts of the electromedical treatment apparatus 1.

Also the electric lens 10 included in the lens system 2 is of the so called square pole type, i.e. also this has four lens elements here called lens electrodes 19-22. Each lens electrode 19-22 consists of an electrically conducting material, for example copper or the like, and is essentially rod-shaped. The surface turned toward the center of the lens system 2 is preferably hyperbolically shaped to maintain the desired field distribution. The lens electrodes 19-22 are symmetrically arranged inside the ring-shaped core 7 of the lens systems 2, in such a way that the two lens electrodes 19-20 with positive potential and the two lens electrodes 21-22 with negative potential are arranged in pairs diametrically opposite each other. The lens electrodes 19-22 that are electrically insulated from the ring shaped core 7 with insulators 25 are advisably arranged displaced with an angle of 45° relative to the lens elements 12-15 contained in the magnetic lens 9. The lens electrodes 21-22 that have a negative potential are connected and wired to the negative terminal of the voltage unit 17 and the lens electrodes 19-20 that have positive potential are connected and wired to the positive terminal of the voltage unit 17. The above described electrical lens 10 diverges the electrically charged particles that pass through its central section.

In the middle of the electromedical treatment apparatus 1, i.e., in its treatment zone, is arranged an electric field of force directed against the magnetic flow. This electrical field of force is generated by an upper and a lower field electrode 6, 5, constituting an electrical field generator 26. The upper field electrode 6 consists of a ringshaped or tube-shaped pipe of metal whereon the pipe end turned toward the treatment zone is hyperbolically shaped. This upper field electrode 6 is supplied with a positive potential, which results in that the flow of the electrical field is directed downwards and cooperates with the gravitational force intended for the electrically charged ions.

The lower field electrode 5 consists in the same way as the upper field electrode 6 of metal and is formed as a ring-shaped pipe. A grid 23 is arranged at its inner edge. This grid 23 consists of bands or rods of tungsten or molybdenum and are arranged in the upper part of the lower field electrode 5. The upper edges of the grid 23 are formed with a sharp eggshaped profile and directed toward the upper field electrode 6. Thus, an electric field is obtained, whose flow is focussed toward the inner part of the lower field electrode 5. This results in a more concentrated field distribution in the treatment zone.

Figure 4:
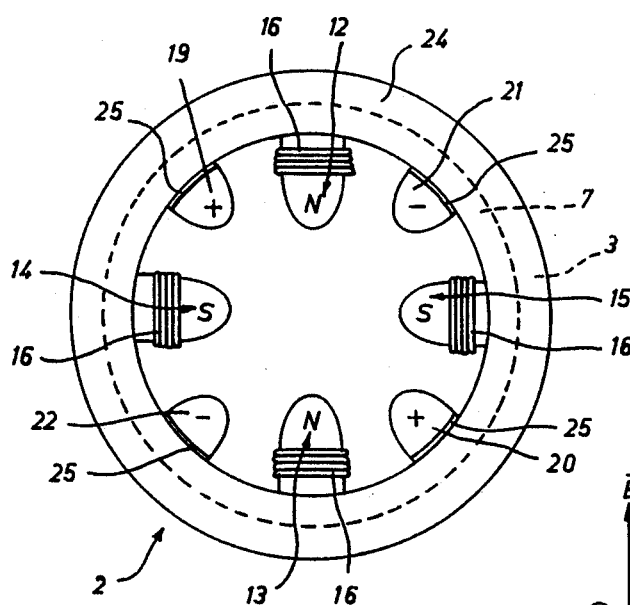
FIG. 4 illustrates schematically a lens system according to the invention.

As is shown in FIGS. 3 and 4 are all solenoids 16 arranged at the lens elements 12-15, are connected in series and all lens electrodes 19, 20 with positive potential are connected together and wired to the positive terminal of the voltage unit 7. The negative lens electrodes 21, 22 are similarly connected to the negative terminal of the voltage unit 17. One and the same voltage unit 17 supplies the entire treatment apparatus 1 with its electrical energy. The voltage consists of a half-wave rectified sinus voltage that never passes zero. The frequency with which the voltage varies is exemplified at to 66 Hz, but can naturally vary between for example 20-100 Hz. Also the amplitude of the voltage is freely adjustable. The voltage to the solenoids 3, 16 can either be positive or negative. It is of course possible to separate the purely electrical system from the electromagnetical system and thereby supply the solenoids 3, 16 on the one hand and the lens electrodes 19-22 and field electrodes 5, 6 on the outer hand with voltages whose parameter values differ. It is, however, desirable that the voltage to both systems vary in accordance with amplitude, frequency and polarity.

In another embodiment, a pipe or a nozzle 27 for gas or liquid additive can be arranged at one or both ends of the electromedical apparatus 1, i.e., coaxially with an imaginary central axis through the lens system 2. Through this pipe or nozzle 27, electrically charged particles possibly mixed with one or more medically active substances, can be supplied to the treatment zone via the one or both lens systems 2.

SHORT THEORETICAL IDEAL MAGNETOHYDRODYNAMICAL BACKGROUND

The function of the invention is based upon generally accepted physical and chemical laws as well as upon new discoveries within the medical research. The theoretical basis is among others collected from the magnetohydrodynamics and the plasmaphysics of Jackson in "Classical Electrodynamics", and the vacuumgaselectronphysics of Lyman Spitzen, Princeton University. In connection with the medical discoveries reference is made to, for example, *Medicine and Biology*, No. 3, 1969.

Plasma waves are high frequency oscillations and must be separated from oscillations of lower frequency, so called magnetohydrodynamic waves, which result in transportation of the media without charge separation. At low frequency the media is contemplated as one (electrons and ions are assumed as one media) conducting media and the movement current in Ampere's law are neglected. This is "magnetohydrodynamics" and is valid among other things for liquids. By means of the laws of Ohm and Maxwell, the magnetic diffusion time, the magnetic pressure, the flowspeed of the liquids and the movement speed of the charged particles in the liquid can be calculated. How the electromedical treatment apparatus is to be constructed to affect the flow of the blood and the ions in the cells and muscle fibres will be shown at the end.

In a perfectly conducting liquid, e.g. blood, the changes caused in the magnetic field are directly proportional to the movement of the liquid. For the magnetic flow that passes through a zone of a sealed circuit (e.g. the bloodflow) the movement of the liquid must be constant. If not, according to Faraday's law of induction, an electromotive force in the circuit will occur. But a perfectly conductive flow cannot maintain an electric field and because of this the electromotive force will disappear. This results in that the force, which influenced a charged particle in the zone, has ceased and the velocity of the flow in the zone decreases.

If an electric field is applied to the zone, the total force, that affects the charged particle will be the sum of the force from the applied field and the Lorentz-force $E^x = E + V \times B$. This force vanishes in a perfect conductor and secures that the magnetic flow remains, i.e. "freezes" in the media.

If the field is not homogeneous in the liquid, but changes over a distance "L", the speed at which the field changes, will be proportional to the speed at which the liquid flows i.e., $$dB/dt \sim vB/L,$$

or if the field has finite resistivity, $$\eta \rightarrow dB/dt \sim \eta B/L^2$$

Through solution of this equation, the time can be achieved, which is necessary for the field to drive into the conducting liquid.

$$t \sim L^{2/\eta}$$

Figure 5A:
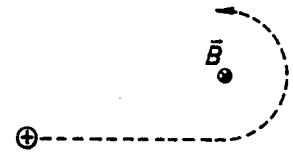
FIG. 5 shows particle paths in force fields.
Figure 5B:
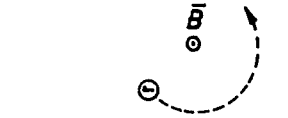
Figure 5C:
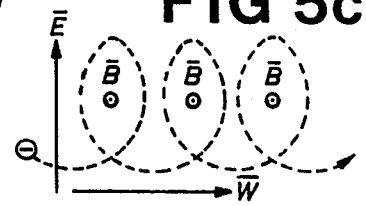

Where:
E = electrical intensity of field
V = velocity
B = magnetic intensity of field
$E^x$ = force
$\eta$ = resistivity FIGS. 5a–c shows paths of charged particles in different fields of force according to accepted laws of nature. E, B and W represent electric field, magnetic field, and mechanical force respectively. In FIG. 5a is shown the movement path of a positive particle in a magnetic field directed "away from the viewer". In FIG. 5b is shown the movement path of a negative particle in a magnetic field directed "toward the viewer". Finally, in FIG. 5c is shown how a negatively charged particle performs a helix-shaped movement in two fields directed perpendicularly against each other. A magnetic field B directed toward the viewer and an electric field E directed upward (as shown by arrows). It is among other things this movement that is achieved by the present invention.

FUNCTION OF THE INVENTION

Our blood, as is known, contains a number of different elements and substances. The most common ions, the so called anions and cations are potassium, sodium, chloride, calcium, iron, sulphate, and phosphate ions. When an ion is a particle whose resultant charge is either positive or negative, it is influenced by electric, electrostatic and magnetic fields. If the ion passes or is in one of these fields movement energy is transmitted to it, so that it starts to move. The mobility or movement velocity of the ion depends among other factors on the viscosity of the surrounding substance. Also the ability of the ion to bring with it other particles in the substance affect the mobility. Convection movements in the substance and density gradients can to some extent also affect the movement of the ion.

In a number of injuries and diseases it has been advantageous to use a treatment that causes hyperaemia, i.e. localized oversupply of blood and increased throughflow of blood. This has so far been achieved by means of physiotherapy, whereby mainly different forms of heating apparatus have been used, such as heating lamps and hing frequency techniques. The increased blood flow which has been achieved in this way, assists the transportation of e.g., nutritional elements, proteins and oxygen to the cells and undissolved products from them. This metabolism supports the healing processes. A substantial drawback during treatment with heating lamps is that the infrared radiation can only pass through a few millimeters in the skin and thereby only affects the body surface.

The electromedical treatment apparatus according to the invention is effective also on deeper lying tissue. This is due to the fact that all positive or negative charged particles in an electric or magnetic field are affected and that these particles are spread in all parts of the tissue.

The electromagnetic radiation is intended to affect the bioelectrical potentials on the cellular plane of the organism—cell membranes and mitochondria etc.—but naturally also will affect water distribution in the organism depending on the special structure of the water molecules. Other organic molecules with dipolar characteristics will probably also be affected.

When voltage is supplied, the treatment apparatus generates on the one hand a magnetic field with a substantially horizontal flow and on the other hand an electric field whose flow is directed transversely to the magnetic flow.

Due to the electric and magnetic lens systems, the magnetic and electric flow will be concentrated in the center of the treatment apparatus, i.e. in its treatment zone. If charged particles, for example the ions in the blood plasma, are supplied in this area they are influenced to move in a determined pattern. The movement velocity of the ions is influenced by the strength of the magnetic and electric fields and bring with them uncharged particles in their immediate surroundings. The strength of the fields is by choice adjustable and can, regarding the strength of the magnetic field, reach for example 2000 Gauss. Both the strength of the magnetic and electric fields vary at the rate of the pulse frequency of the introduced voltage. A pulse frequency of 66 Hz has been shown to coincide with the biological activity of the body but can, when needed, be adjusted between 20–80 Hz.

By locating the relevant body part, for example an arm or a leg, in the treatment apparatus substantially perpendicular to both the magnetic and electric field so that both lens systems transmit force components to the ions in the body part, the ions are helically moved in the direction of the length of the blood vessels (see FIG. 5c). When substantially all charged particles receive an equal movement component and each charged particle to a greater or lesser extent brings with it other, uncharged closely lying particles, an increased flow through of blood in the vessels is obtained.

The energy transferred to the ion results in a movement which in short can be described in the following way. A positively charged particle that approaches a magnetic field will curve and rotate counter-clockwise seen in the view of the direction of the flow of the magnetic field. If an electric field is applied perpendicular to the magnetic field and the flow of the electric field is directed upward, the positively charged particle will accelerate on the right side of the magnetic field and slow down on the left. If the particle is negatively charged, the relationship will be the opposite. The final movement path will be helical, i.e. screwformed, with a constant pitch. This is visualized in FIG. 5c.

When the charged particles start to move and thereby bring with them close-lying particles, an advantageous increase of the blood throughflow is obtained in the treated tissue. Also an analgesic, i.e., pain reducing, effect can be shown. Pain depends on lack of oxygen in the tissues or of a collection of pain substances. An increase of the blood flow gives increased oxygen supply and supports the removal of the pain substances.

Since also the central nervous system works by means of electrically charged particles which pass in and out of the nerve cells and in this way transmit information, to for example the muscles, neurologically caused wounds or diseases can be treated with the electromedical treatment apparatus according to the invention. An example of this is that certain types of handicaps, such as neurologically caused movement restrictions, can be treated.

A large part of diseases of older persons stem from the circulatory system and its peripheries. Within this diseases area it is difficult to produce adequate medicine because the side effects on other organs increase, especially so on older persons. There exists therefore a clear need for an alternative technique that limits its affect on the cellular plane to the diseased organ.

Many persons suffer from so called deliming of the skeleton when they get older. This greatly increases the risks of fractures, where femur breakage is a common injury. The treatment period for this type of injury can be very long and consume a large part of medical service resources. With the electromedical treatment apparatus according to the invention a quicker healing is achieved when treating these femur breaks. It has been shown that calcium ions can be forced to wander back into the skeleton whereby a delimed skeleton can be regenerated. In this way bone fractures also can be prevented.

The healing of leg wounds, burns and slow-healing, infected sores can also be speeded up with the treatment apparatus according to the invention. This can for example be carried out by supplying a medically active substance such as active iodine, or antibiotics in mist form, to the treatment zone by acceleration from one or both of the lens systems 2 via for example a nozzle 27. This is also the case with hyperbar oxygen therapy. A bombardment of the wound with the medically active substances can thereby be achieved. Due to this method of treatment the otherwise developing resistant infection causes can be avoided.

I claim:

1. An apparatus for electromedically treating biological tissues by inducing the directed movement of electrically charged particles in said tissues, comprising:

magnetic field generating means for generating a magnetic field with regularly varying field strength in a treatment zone, in which treatment zone may be positioned a body part or the like to be treated, the generated magnetic field in said treatment zone being horizontally directed by said magnetic field generating means so as to be substantially perpendicular to a central axis of said treatment zone;

electric field generating means for generating an electrical field of regularly varying field strength in said treatment zone, the generated electric field in said treatment zone being vertically directed by said electric field generating means so as be substantially transverse to the magnetic field generated in said treatment zone by the magnetic field generating means, said generated electric field in said treatment zone being also directed by said electric field generating means so as to be substantially perpendicular to the central axis of said treatment zone; and power source means for supplying a regularly varying voltage to said magnetic field generating means and electric field generating means, the strengths of the generated magnetic and electrical fields varying at the same rate as said supplied voltage;

said generated magnetic field and said generated electric field impressing respectively perpendicularly directed magnetic and electrical field forces in said treatment zone for inducing the directed movement of charged particles in said treatment zone with respect to the directions of said magnetic and electric fields.

2. The apparatus according to claim 1, wherein the magnetic field generating means comprises:

a pair of generally ring-shaped magnetic lenses coaxially arranged and spaced-apart from one another on opposite sides of said treatment zone along a common central horizontal axis passing through said treatment zone, each said magnetic lens including a generally annular core disposed concentrically about said common horizontal axis, a first solenoid coil being wound about a circumference of said core and electrically connected to said power source means and to the solenoid coil of the other magnetic lens system, each said magnetic lens further including four magnetic lens elements symmetrically arranged in diametrically opposing pairs within an inner space of each core for constituting magnetic pole pieces, said magnetic lens elements being each provided with a second solenoid coil therearound connected to said power source and to other ones of said second solenoid coils such that a pair of diametrically opposed north magnetic pole pieces and a pair of diametrically opposed south magnetic pole pieces are provided in each magnetic lens; and an electric lens provided in each of said magnetic lenses, each said electric lens including four electric lens elements symmetrically arranged in diametrically opposing pairs inside said core and displaced angularly relative said magnetic lens elements, said electrical lens elements being connected to said power source means so as to constitute a pair of diametrically opposed positive electrodes and a pair of diametrically opposed negative electrodes;

wherein each said magnetic lens operates to converge electrically charged particles in and passing through a central section thereof, and each said electric lens operates to diverge electrically charged particles passing through a central section thereof.

3. The apparatus according to claim 1, wherein said electric field generating means comprises an upper field electrode connected to said power source means and supplied therefrom with a positive potential, and a lower field electrode connected to said power source means and supplied therefrom with a negative potential, said upper and lower field electrodes being arranged coaxially and respectively opposed above and below said treatment zone along a common central vertical axis passing through said treatment zone, said upper and lower field electrodes being disposed substantially equidistant along said common central vertical axis with respect to a central horizontal axis of said magnetic field generating means passing through said treatment zone, whereby a downwardly-directed electric field passing through said treatment zone is generated between said upper and lower field electrodes.

4. The apparatus according to claim 2, further comprising at least one nozzle means coaxial with the central horizontal axis of said magnetic lenses for supplying charged particles or medically active substances to said treatment zone.

5. The apparatus according to claim 3, wherein said upper and lower field electrodes are substantially tubular and have respective hyperbolically-formed ends facing the treatment zone.

6. The apparatus according to claim 3, wherein said upper and lower field electrodes have respective rounded facing ends.

7. The apparatus according to claim 3, wherein an inner edge of an end of one of said upper and lower field electrodes facing the treatment zone is provided with a grid for focussing the electric field flow toward an inner part of said field electrode.

* * * * *